United States Patent [19]
Postma

[11] Patent Number: 4,572,007
[45] Date of Patent: Feb. 25, 1986

[54] THERMOPHORETIC SEPARATION OF AEROSOL PARTICLES FROM A SAMPLED GAS STREAM

[75] Inventor: Arlin K. Postma, Halfway, Oreg.

[73] Assignee: The United States of America as represented by the United States Department of Energy, Washington, D.C.

[21] Appl. No.: 648,197

[22] Filed: Sep. 7, 1984

[51] Int. Cl.[4] .............................................. G01N 1/22
[52] U.S. Cl. .................................... 73/863.12; 55/16; 55/81; 55/158; 55/209
[58] Field of Search .................. 73/19, 863.11, 863.12, 73/863.21, 863.23; 55/16, 158, 267, 81, 209

[56] References Cited

U.S. PATENT DOCUMENTS

| 1,174,631 | 3/1916 | Snelling. | |
|---|---|---|---|
| 2,701,467 | 2/1955 | Strong | 55/209 |
| 2,824,620 | 2/1958 | Rosset | 55/16 |
| 3,552,211 | 1/1971 | Dollinger | 73/863.12 |
| 3,630,690 | 12/1971 | Coppola | 55/16 |
| 3,853,504 | 12/1974 | Buscher. | |
| 3,866,460 | 2/1975 | Pearce. | |

Primary Examiner—S. Clement Swisher
Attorney, Agent, or Firm—Robert Southworth, III; Judson R. Hightower

[57] ABSTRACT

A method for separating gaseous samples from a contained atmosphere that includes aerosol particles uses the step of repelling particles from a gas permeable surface or membrane by heating the surface to a temperature greater than that of the surrounding atmosphere. The resulting thermophoretic forces maintain the gas permeable surface clear of aerosol particles. The disclosed apparatus utilizes a downwardly facing heated plate of gas permeable material to combine thermophoretic repulsion and gravity forces to prevent particles of any size from contacting the separating plate surfaces.

11 Claims, 5 Drawing Figures

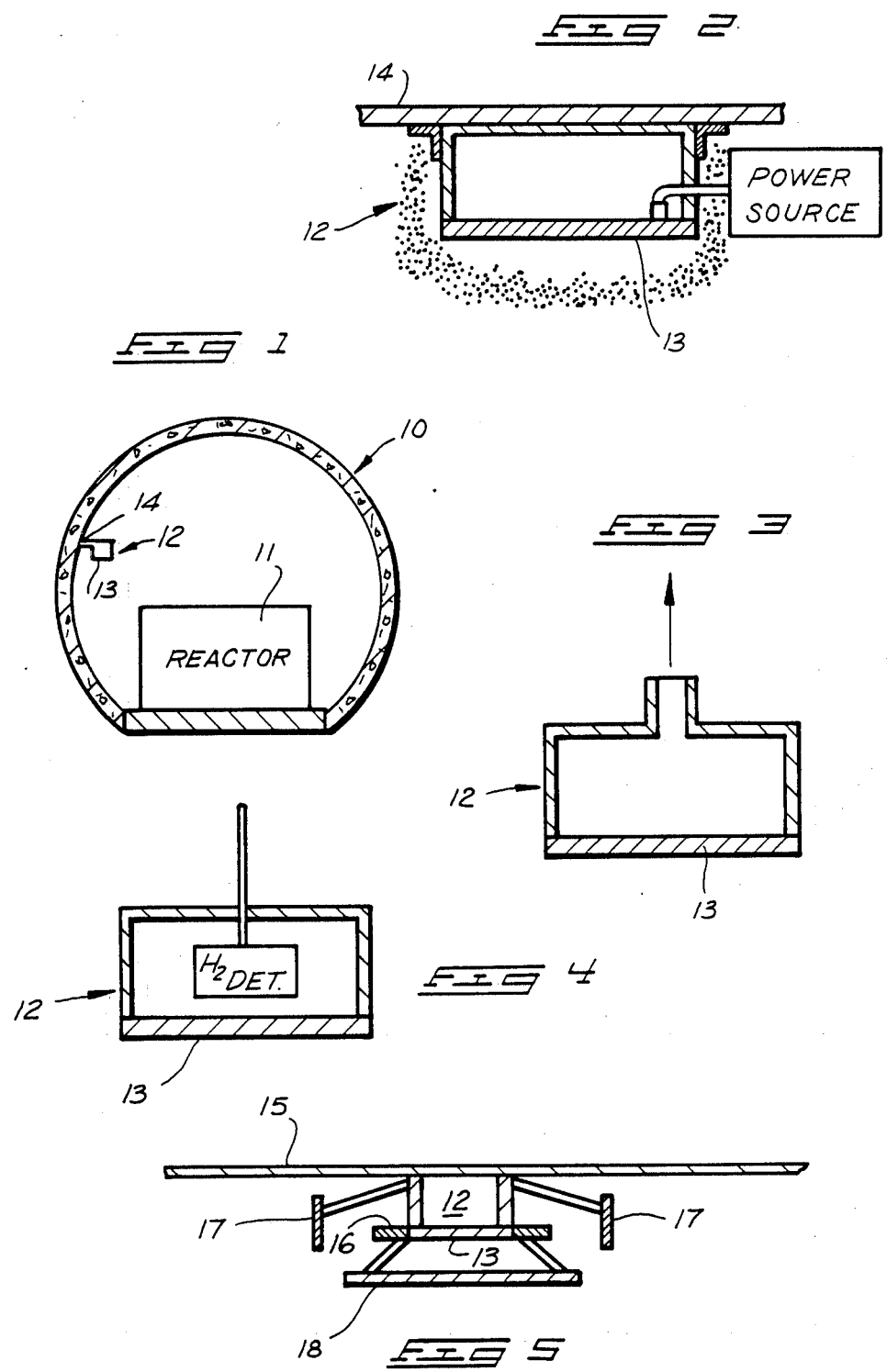

4,572,007

THERMOPHORETIC SEPARATION OF AEROSOL PARTICLES FROM A SAMPLED GAS STREAM

The United States Government has rights in this invention pursuant to contract DE-AC14-76FF02170 between the U.S. Department of Energy and Westinghouse Electric Corporation.

BACKGROUND OF THE INVENTION

This disclosure relates to separation of aerosol particles from gas samples withdrawn from within a contained atmosphere, such as containment vessels for nuclear reactors or other process equipment where remote gaseous sampling is required. It is specifically directed to separation of dense aerosols including particles of any size and at high mass loadings and high corrosivity.

This invention arose from efforts to withdraw gaseous samples from atmospheres simulating those which would be predicted to exist in a containment building or vessel for a liquid metal cooled breeder reactor following a postulated melt-through accident. Dense aerosols, having concentrations of up to 100 $g/m^3$, at temperatures up to 1000° F. and consisting of a number of sodium compounds (including NaOH), have been postulated. These aerosols must be removed from gas samples which are to be analyzed for hydrogen content. Both the high mass loadings and the corrosive properties of the aerosols greatly limit the performance of conventional filtering means for their removal.

SUMMARY OF THE INVENTION

It is an object of this invention to provides a new and useful method for separating aerosol particles within the confines of a containment building or vessel.

Another object of this invention is to provide an apparatus which assures effective gaseous separation without direct contact of gas permeable surfaces by surrounding aerosol particles of any size.

To achieve the foregoing and other objects, and in accordance with the purposes of the present invention as embodied and broadly described herein, the method of this invention comprises the steps of placing within the contained atmosphere a gas impermeable enclosure having an interior chamber partly defined by a bottom metal plate that is permeable to gas, fixing the position of the enclosure with the plate facing downwardly and exposed to the contained atmosphere, heating the metal plate above the temperature of the contained atmosphere to produce an outward temperature gradient which, together with gravitational forces, prevents contact of aerosol particles with the downwardly facing surfaces of the heated metal plate, and sampling gas found in the interior chamber of the enclosure.

The present apparatus is in the form of a covering gas impermeable enclosure having an interior chamber partly defined by a bottom metal plate that is gas permeable, means for fixing the enclosure within a containment structure with the metal plate facing downwardly and directly exposed to the atmosphere being sampled, means for heating the metal plate to a temperature above that of the atmosphere being sampled to thereby produce a temperature gradient capable of exerting downward forces on aerosol particles adjacent to the metal plate, and means for sampling gas within the interior chamber of the enclosure.

BRIEF DESCRIPTION OF THE DRAWINGS

The accompanying drawings, which are incorporated into and form a part of the specification, illustrate an embodiment of the present invention and, together with the description, serve to explain the principles of the invention. In the drawings:

FIG. 1 is a schematic view of a containment structure and gas sampling apparatus;

FIG. 2 is an enlarged schematic view of the gas separating apparatus, illustrating its operation;

FIG. 3 is a simplified schematic view showing a separation apparatus for in situ measurements of hydrogen;

FIG. 4 is a similar simplified schematic view showing a separating apparatus adapted for remote gas detection; and FIG. 5 is a schematic view of the gas separating apparatus and auxiliary shields.

DESCRIPTION OF THE PREFERRED EMBODIMENT

This disclosure relates to a method and apparatus for separating gaseous samples from an atmosphere containing aerosols. While it arose from design efforts relating to analysis of gaseous samples containing high loadings of corrosive aerosols that would result from an operational accident in a nuclear reactor, it is applicable to gas sampling requirements in many other applications as well. It generally pertains to gaseous sampling from aerosols located within a protective containment structure, such as an enclosed building or vessel where atmospheric currents arise mainly from natural convection.

The approach of this disclosure is based on thermophoretic repulsion of aerosol particles. Thermophoresis can be generally defined as motion of a particle due to a temperature gradient in the atmosphere surrounding the particle. The present disclosure utilizes the concept of thermophoretic repulsion of aerosol particles in conjunction with gravitational forces to maintain a gas permeable surface substantially free from contact by aerosol particles of any size or composition.

FIG. 1 schematically shows a containment structure 10 in the form of a pressure vessel containing a nuclear reactor 11. In the event of an accident, the interior of the structure 10 would be subjected to mass loadings of corrosive aerosols which could inhibit gaseous sampling of the atmosphere within structure 10. Periodic gaseous sampling to determine hydrogen content is important to the monitoring of conditions within the containment structure.

According to this invention, gaseous samples can be drawn from within the containment structure 10 by placing within the contained atmosphere a covering gas impermeable enclosure 12 having an interior hollow chamber partly defined by a bottom plate 13 that is gas permeable. As can be seen in FIG. 2, the hollow interior of enclosure 12 is exposed directly to the upwardly facing surface of plate 13. The enclosure 12 is fixed within the containment structure 10 with plate 13 facing downwardly and directly exposed to the contained atmosphere within structure 10.

By heating the metal plate 13 to a temperature greater than that of the atmosphere within the containment structure 10, aerosol particles in the contained atmosphere will be repelled by the resulting thermophoretic forces applied to them by the temperature gradient produced in the atmosphere immediately under the plate. Gravity forces augment these thermal forces on the aerosol particles and prevent larger particles from contacting the downwardly facing surfaces as such larger particles drop about the enclosure 12.

There is no precise range of elevated temperatures required for operation of plate 13 in repelling aerosol particles. As a specific example, separation has been experimentally observed by use of a downwardly facing plate heated to a temperature approximately 100° F. above the temperature of the surrounding atmosphere.

The present method can be used for in situ measurement of the hydrogen content of the atmosphere within the containment structure 10 by using diffusion separation of hydrogen from other gases through a solid heated plate of platinum or a platinum alloy that is permeable only to hydrogen. Alternatively, a gas permeable metal plate can be used to permit infiltration of all gaseous materials to the interior of enclosure 12 for remote analysis of hydrogen content (FIG. 4).

The apparatus essentially comprises the covering gas impermeable enclosure 12, the gas permeable plate 13, and brackets 14 or other means for fixing enclosure 12 within the containment structure 10 in a stationary position with the metal plate 13 facing downwardly and directly exposed to the atmosphere within the containment structure 10.

The precise design of the enclosure 12 and plate 13 will be dependent upon the expected atmospheric conditions within the receiving containment structure 10. For a containment atmosphere having appreciable convection currents, the heated plate 13 would require shielding as generally shown in FIG. 5. This could be effectively provided by a group of baffles or solid plates designed to maintain the lower surface of heated plate 13 free from atmospheric currents which could produce turbulence and which might overcome the thermal forces which repel the aerosol particles.

FIG. 5 schematically shows a covering roof plate 15 radiating outwardly from the top surfaces of enclosure 12, a similarly radiating guard plate 16 extending outwardly from the heated plate 13, a spaced circumferential annular ring 17 surrounding the metal plate 13, and a lower protective floor plate 18. The plate 18 would be vertically spaced from the lower surfaces of heated plate 13 by a distance greater than the expected vertical accumulation of particles that might be deposited on the floor plate during use of this equipment.

The above method and apparatus provides effective separation of suspended aerosol particles with relatively little dependence upon the physicochemical properties of the particles. Operation of the system is not limited by the size of these suspended particles, their composition, or their concentration. The apparatus is physically small in comparison to the size of the containment structure within which it is utilized, and rigid, with no moving parts or other elements requiring periodic maintenance. It can be made entirely of materials capable of tolerating extremely high temperatures. Its power requirements are quite low, being only that necessary to provide an effective temperature gradient beneath the heated metal plate 13. The components of the equipment will not deteriorate with age and the cost of the equipment should be relatively minimal.

The foregoing description of the Preferred Embodiment of the invention has been presented for purposes of illustration and description. It is not intended to be exhaustive or to limit the invention to the precise method steps or apparatus disclosed. Obviously, many modifications and variations are possible in view of the above teaching. The embodiment of the method and apparatus in detail was chosen and described in order to best explain the principles of the invention and its practical application so as to enable others skilled in this art to best utilize the invention. It is contemplated that various embodiments and modifications suited to a particular use will be utilized. It is intended that the scope of the invention be defined by the claims attached to this disclosure.

I claim:

1. A method for separating aerosol particles from a gas sample being withdrawn from a contained atmosphere, comprising the following steps:
    placing within the contained atmosphere a covering gas impermeable enclosure have an interior chamber partly defined by a bottom metal plate that is permeable to gas;
    fixing the position of the enclosure with the plate facing downwardly and directly exposed to the contained atmosphere;
    heating the metal plate to a temperature greater than that of the contained atmosphere, whereby aerosol particles are repelled to the resulting thermophoretic forces applied to them by the temperature gradient produced in the atmosphere immediately under the plate;
    and sampling gas within the interior chamber of the enclosure.

2. A method as set out in claim 1, comprising the following step:
    determining the hydrogen content of the gas within the interior chamber of the enclosure.

3. A method as set out in claim 1, comprising the following step:
    selecting a metal plate of material permeable only to hydrogen;
    and directly measuring the hydrogen content of gas within the interior chamber of the enclosure.

4. A method as set out in claim 1, comprising the following step:
    withdrawing gaseous samples from the interior chamber chamber of the enclosure for subsequent measurement of hydrogen content.

5. A method as set out in claim 1 further comprising the step of arranging protective solid plates about the heated plate to shield its exposed surfaces from surrounding convection currents within the contained atmosphere.

6. An apparatus for separating aerosol particles from a gas sample being withdrawn from within a containment structure, comprising:
    a covering gas impermeable enclosure having a bottom metal plate that is permeable to gas, said enclosure and plate encompassing a hollow chamber for reception of a gas sample;
    means for fixing the enclosure within the containment vessel in a stationary position with its metal plate facing downwardly and directly exposed to the atmosphere within the containment structure; and
    means for heating the metal plate to a temperature above that of the atmosphere within the containment vessel to produce a temperature gradient in the atmosphere immediately adjacent the exposed surfaces of the metal plate, exerting a downward force on particles exposed to the temperature gradient beneath the metal plate.

7. An apparatus as set out in claim 6 wherein the metal plate is constructed from a material permeable only to hydrogen.

8. An apparatus as set out in claim 7 further comprising:
 hydrogen detector means positioned within the interior chamber of the enclosure for directly measuring the hydrogen content of gas within the enclosure.

9. An apparatus as set out in claim 6 wherein the enclosure is further provided with a protruding plate radiating outward about the enclosure as an extension of the metal plate.

10. An apparatus as set out in claim 6 wherein the enclosure is further provided with an annular ring surrounding the metal plate.

11. An apparatus as set out in claim 6 further comprising:
 solid plate means fixedly arranged about the enclosure and metal plate for shielding the exposed surfaces of the metal plate from surrounding convection currents within the containment vessel.

* * * * *